(12) United States Patent
Nusstein

(10) Patent No.: US 6,948,935 B2
(45) Date of Patent: Sep. 27, 2005

(54) ULTRASONIC DENTAL DEVICE

(75) Inventor: John Nusstein, Dublin, OH (US)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 10/334,423

(22) Filed: Dec. 30, 2002

(65) Prior Publication Data

US 2004/0126732 A1 Jul. 1, 2004

(51) Int. Cl.[7] ............................................. A61C 3/03
(52) U.S. Cl. ........................ 433/119; 433/224; 433/118; 433/120
(58) Field of Search .................. 433/102, 119, 433/165, 166, 224, 118, 120, 121–124; 601/162, 163, 164, 165

(56) References Cited

U.S. PATENT DOCUMENTS

| | | | |
|---|---|---|---|
| 4,019,254 A | | 4/1977 | Malmin |
| 4,229,168 A | | 10/1980 | Scholz, Jr. |
| 4,492,574 A | | 1/1985 | Warrin et al. |
| 4,505,676 A | | 3/1985 | Gonser |
| 4,617,918 A | * | 10/1986 | Donohue et al. ............ 601/162 |
| 4,681,545 A | | 7/1987 | Lapcevic |
| 4,818,229 A | | 4/1989 | Vasile |
| 5,116,227 A | | 5/1992 | Levy |
| 5,320,530 A | | 6/1994 | Fong |
| 5,567,153 A | | 10/1996 | Foulkes et al. |
| 5,868,570 A | | 2/1999 | Hickok et al. |
| 6,050,818 A | * | 4/2000 | Boland et al. ............... 433/118 |
| 6,162,202 A | | 12/2000 | Sicurelli et al. |
| 2003/0207231 A1 | * | 11/2003 | Nance ......................... 433/81 |

OTHER PUBLICATIONS

Archer et al.; An in vivo evaluation of the efficacy of ultrasound after step–back preparation of mandibular molars. Journal of Endodontics: vol. 18, No. 11, pp. 549–552 (Nov. 1992). Published by the American Association of Endodontists.

Haidet et al.; An in vivo comparison of the step–back technique versus a step–back/ultrasonic technique in human mandibular molars. Journal of Endodontics: vol.15, No. 5, pp. 195–199 (May 1989). Published by the American Association of Endodontists.

*Primary Examiner*—Pedro Philogene
*Assistant Examiner*—Candice C. Stokes
(74) *Attorney, Agent, or Firm*—Calfee, Halter & Griswold LLP

(57) ABSTRACT

A device for performing endodontic procedures such as root canals by utilizing ultrasonic energy to debride the root canal space. The device includes a modified shaft assembly and a stainless steel hypodermic needle which concentrates the ultrasonic energy at the tip of the needle. The shaft assembly further includes a threaded housing for attaching the shaft assembly to an ultrasonic generator, an angled shaft attached to the threaded housing, and a hub attached to the end of the angled shaft opposite the threaded housing for reducing the diameter of the bore when the hub is tightened. The angled shaft further includes a bore passing through its length and an aperture passing through the outer wall of the shaft. The aperture is positioned near the larger of the two angles formed by the angled shaft and is oriented in the direction of the hub. The needle is inserted into the aperture and passes through the bore in the angled shaft until it exits the shaft through the hub. The working length of the needle may be adjusted by the practitioner.

7 Claims, 2 Drawing Sheets

OTHER PUBLICATIONS

Lev et al.; An in vivo comparison of the step–back technique versus a step–back/ultrasonic technique for 1 and 3 minutes. Journal of Endodontics: vol. 13, No. 11, pp. 523–530 (Nov. 1987). Published by the American Association of Endodontists.

Goodman et al.; An in vitro comparison of the efficacy of the step–back technique versus a step–back/ultrasonic technique in human mandibular molars. vol. 11, No. 6, pp. 249–256 (Jun. 1985). Published by the American Association of Endodontists.

* cited by examiner

ULTRASONIC DENTAL DEVICE

TECHNICAL FIELD OF THE INVENTION

The present invention relates generally to devices for performing dental procedures, and specifically to an ultrasonic device useful for performing certain dental procedures such as root canal therapy, i.e., endodontics.

BACKGROUND OF THE INVENTION

Performance of endodontic therapeutic techniques on the dental patient typically requires the proper debridement of the root canal space by the dental practitioner. As the root canal is debrided and enlarged, substrates within the tooth that may be suitable for the growth of microorganisms are reduced. Furthermore, dental practitioners have long recognized the importance of completely removing all organic matter from the root canal of the tooth prior to filling the root canal with medication or other material. Failure to properly debride the root canal space and to completely remove all organic matter from the same space can result in inflammation and infection. Such inflammation and/or infection may require the endodontic therapy to be repeated or the tooth to be removed. Either outcome is undesirable for the dental patient and for the dental practitioner.

A variety of tools currently exist for the application of endodontic therapy. Such endodontic tools include broaches, reamers and files, all of which typically include a base having a relatively larger diameter that tapers to a tip having a relatively small diameter. Applying ultrasonic energy to such devices, especially files, is known by those skilled in the art of dentistry to increase the effectiveness of such devices; however, certain structural features, weaknesses, or other deficiencies in the materials used to make these tools often causes the devices to fracture or break when ultrasonic energy is directed into and through them. Because the use of ultrasonic energy potentially provides the dental practitioner with certain advantages, such as (i) improved cleaning and disinfection of the root canal space, and (ii) improved or enhanced placement of medicaments, sealers and obturating materials, there is a need for a durable and inexpensive substitute for the files and other devices that are currently used in combination with ultrasonic generators for endodontic procedures.

SUMMARY OF THE INVENTION

These and other deficiencies of the prior art are overcome by the present invention which provides a device for performing endodontic procedures such as root canals. The dental device of the present invention utilizes ultrasonic energy and, preferably, includes a shaft assembly and a stainless steel hypodermic needle which directs and concentrates the ultrasonic energy at the tip of the needle. An exemplary embodiment of the shaft assembly further includes a threaded housing for attaching the shaft assembly to an ultrasonic generator, an angled shaft attached to the threaded housing, and a hub attached to the end of the angled shaft opposite the threaded housing for reducing the diameter of the bore when the hub is tightened. The angled shaft further includes a bore passing through its length and an aperture passing through the outer wall of the shaft. Preferably, the aperture is substantially oval in shape and is positioned near the larger of the two angles formed by the angled shaft and is oriented in the direction of the hub. In the exemplary embodiment, the needle is inserted into the aperture and passes through the bore in the angled shaft until it exits the shaft through the hub. The needle is secured within the bore by tightening the hub at the end of the angled shaft. The working length of the needle is variable and may be adjusted to an optimal length by the practitioner.

The present invention further includes a means, i.e., an assembly, for delivering fluid into and through the needle while the ultrasonic generating unit is being used by the dental practitioner. This assembly includes a reservoir, such as a syringe, for storing the fluid, and a tubing assembly which includes a length of tubing and a means for connecting the tubing to the reservoir and the needle. The use of ultrasonic energy with the present invention provides the dental practitioner with numerous advantages, including improved distribution and placement of fluids, as well as a reduction in the time required for the placement of medicaments, medications, sealers, and obturating materials.

Further advantages of the present invention will become apparent to those of ordinary skill in the art upon reading and understanding the following detailed description of the preferred embodiments.

BRIEF DESCRIPTION OF THE DRAWINGS

The accompanying drawings, which are incorporated into and form a part of the specification, schematically illustrate an exemplary embodiment of the present invention and, together with the general description given above and detailed description of the preferred embodiments given below, serve to explain the principles of the invention.

DETAILED DESCRIPTION OF THE INVENTION

Figure 1:
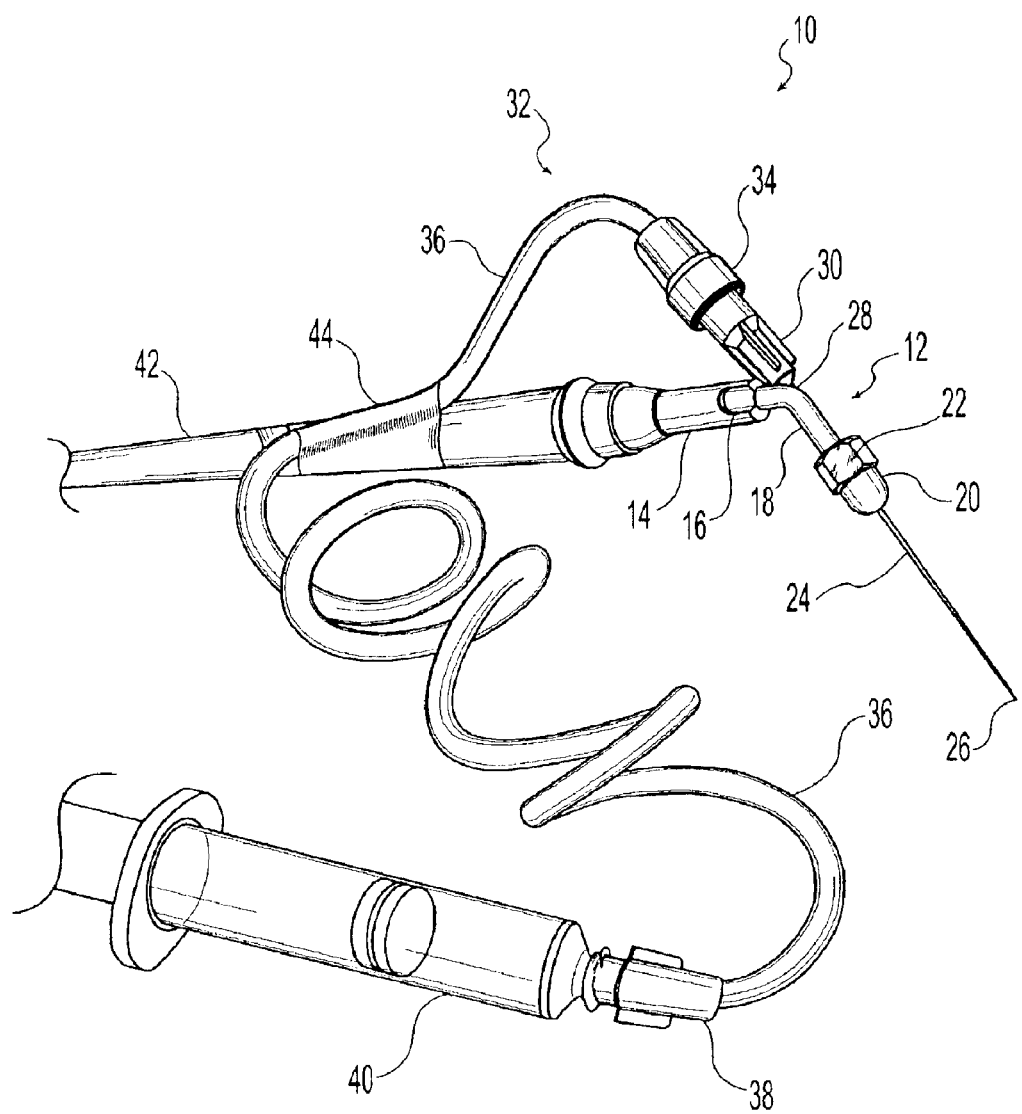
FIG. 1 is a perspective view of the dental device of the present invention showing both the shaft assembly and the tubing assembly.
Figure 2:
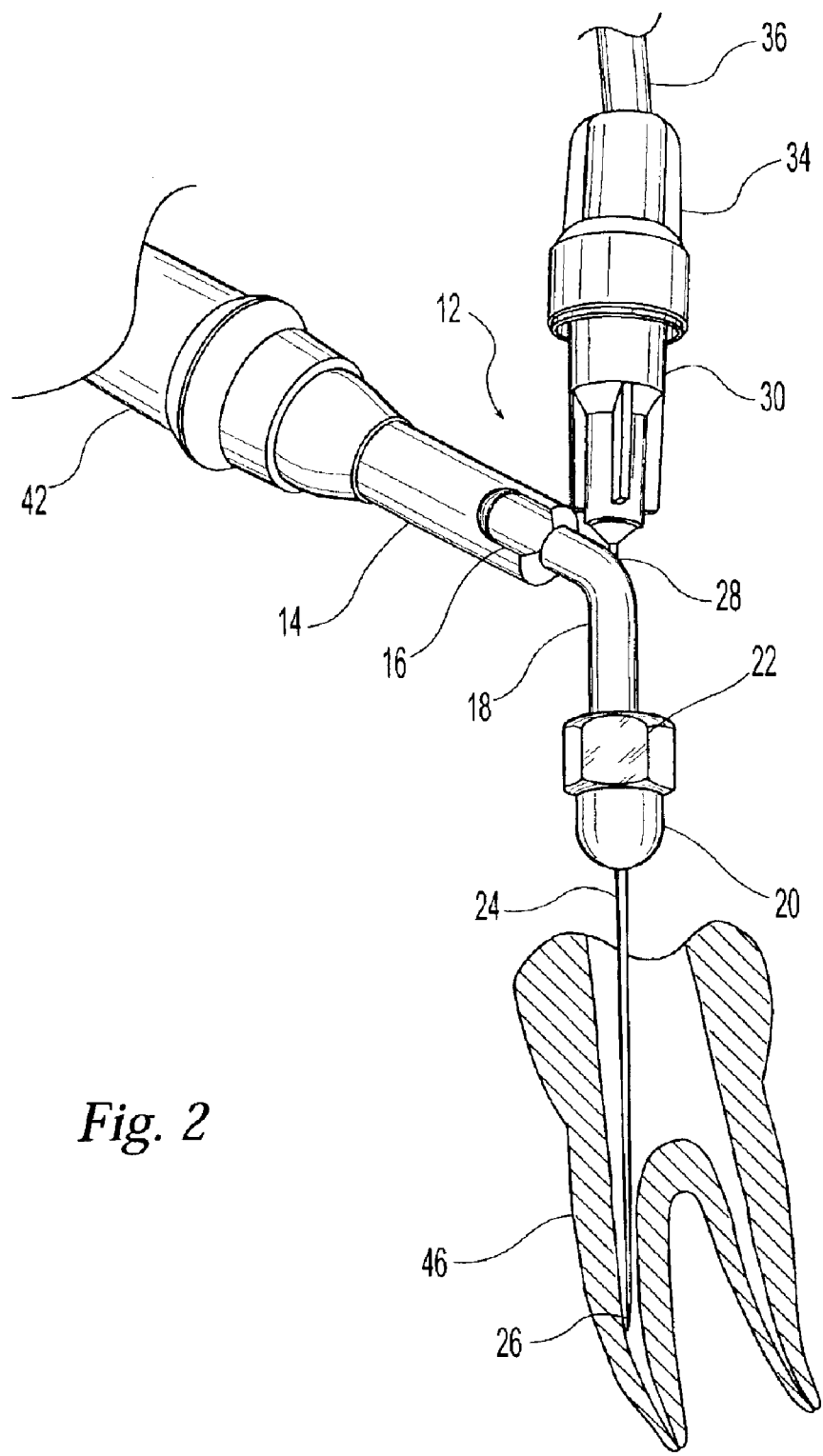
FIG. 2 is a perspective view of the dental device of FIG. 1 showing the operative part of the device of FIG. 1 being used to perform a root canal.

Reference Numerals
10 dental device
12 shaft assembly
14 threaded housing
16 first planar surface
18 shaft
20 hub
22 second planar surface
24 needle
26 tip
28 aperture
30 connector
32 tubing assembly
34 first collar
36 length of tubing
38 second collar
40 syringe
42 ultrasonic wand
44 attachment means
46 tooth With reference to the Figures, and according to an exemplary embodiment of the present invention, dental device 10 includes a shaft assembly 12, needle 24, tubing assembly 32, syringe 40, and ultrasonic wand 42. As illustrated in FIGS. 1 and 2, shaft assembly 12 further includes a threaded housing 14, first planar surface 16, shaft 18, hub 20, and second planar surface 22. First planar surface 16 is threadably attached to ultrasonic wand 42 when dental device 10 is in operation. Threaded housing 14 further includes a first planar surface 16 on either side of the housing. This first planar surface is compatible with a commercially available key-like tool (not shown), that is used tighten shaft assembly 12 to ultrasonic wand 42. In an exemplary embodiment, shaft 18 is angled downward (i.e., toward the patient when in use) at an angle of about 30° to 90°. Hub 20 is attached to the end of shaft 18 opposite the end attached to threaded housing 14. Hub 20 further includes a second planar surface 22 on either side of the hub body. This second planar surface is also compatible with a commercially available key-like tool (not shown) that is used to tighten hub 20 onto shaft 18. Shaft 18 includes a bore running through its length. By tightening hub 20, the bore running through the length of shaft 18 is compressed to a slightly smaller diameter, thereby providing a means for securing a needled within the bore of shaft 18.

In the exemplary embodiment of this invention, shaft 18 further includes aperture 28 which is drilled through shaft 18 on the side of the shaft having the larger of the two angles (see FIG. 1). Preferably, this aperture is substantially oval in shape and is positioned such that tip 26 of needle 24 can be inserted into the aperture and directed through the bore within shaft 18 and out of the end of shaft 18 where hub 20 is attached without bending the body of needle 24 to any appreciable extent (see FIGS. 1 and 2). Preferably, needle 24 is any of a variety of commercially available hypodermic needles that are substantially non-flexible in nature and that include a sharpened tip at one end. Preferably, the end of needle 24 opposite tip 26 includes a connector 30 that permits needle 24 to be attached to a syringe, length of tubing, or other items or devices.

As shown in FIGS. 1 and 2, dental device 10 further includes tubing assembly 32 which permits fluid to be delivered from a reservoir to the site within a dental patient's mouth where dental device 10 is being utilized. After needle 24 has been inserted through shaft 18, first collar 34 is attached to connector 30 and second collar 38 is attached to a fluid reservoir such as a syringe (see FIG. 1). In an exemplary embodiment, a length of tubing 36 runs between the two collars and provides the conduit for the passage of fluid from the reservoir to the patient's mouth. As shown in FIG. 1, a syringe having a Luer-Lok ® type connector is preferred as the reservoir for fluids because the operator of dental device 10 can easily control the volume of fluid delivered into and through tubing assembly 32.

The exemplary embodiment of the present invention may be assembled from commercially available components, and these components may be manufactured from a variety of materials including metals and plastics. For example, shaft assembly 12 is typically manufactured from stainless steel or a similar metal or alloy. Needle 24 is typically manufactured from stainless steel. Tip 26 may be single, bi-beveled, tri-beveled, or may be manufactured by any process that creates a sharp point such that ultrasonic energy can be direct to and focused at the tip of the needle. Preferably, needle 24 is substantially rigid, i.e., non-flexible, and does not bend to any significant degree when inserted into shaft assembly 12. Tubing assembly 32 is typically manufactured from plastic or a similar material, as is syringe 40, although other materials are compatible with these components of the present invention.

Prior to use, dental device 10 must be properly assembled. An exemplary method for assembling dental device 10 includes the following steps. First, shaft assembly 12 is threaded onto ultrasonic wand 42 which includes a threaded attachment means for receiving shaft assembly 12. As will be appreciated by those skilled in the art, ultrasonic wand 42 is typically attached to a separate power supply and may be any of a variety of ultrasonic devices that are commercially available. Second, needle 24 is inserted into shaft 18 through aperture 28 and the length of the needle is adjusted to correspond to the endodontic working length or similar pre-determined length derived by using a millimeter rule or other method used by those skilled in the dental arts. Third, hub 20 is tightened around shaft 18 to secure the needle within the shaft. Fourth, one end of tubing assembly 32 is attached to connector 30 and the other end of the tubing assembly is attached to syringe 40. A portion of the tubing 36 may be secured to ultrasonic wand 42 by attachment means 44 as shown in FIG. 1. Suitable materials for attachment means 44 include a length of plastic or cloth tape.

Once dental device 10 has been assembled as described above, needle 24 is placed within the root canal in tooth 46 to an appropriate length (see FIG. 2). The ultrasonic device is activated by the user at a power level ranging from low to the maximum power. Ultrasonic energy passes from the ultrasonic wand into the shaft assembly, travels down the length of the needle, and is concentrated and focused at the tip of the needle. As ultrasonic energy is directed through the needle and into the root canal, a fluctuating pressure-vacuum field known as transient and stable cavitation is generated. As will be appreciated by those skilled in the art, this energy field destroys microorganisms present within the root canal and loosens tissue and other debris from the affected area, thereby allowing for a more complete endodontic treatment.

While the needle is operating in ultrasonic mode, an irrigating solution, stored in the syringe or other reservoir, may be dispensed into the root canal by depressing the plunger on the syringe or by actuating a pump if another type of reservoir is being used. This solution washes out the affected area within the root canal and effectively removes loosened tissue, microorganisms, and other debris. By way of example, solutions of sodium hypochlorite, sterile saline, chlorhexidine, citric acid, calcium hydroxide, antibiotic solutions, antiseptic solutions, demineralizing solutions or a combination of these solutions may be used as irrigating solutions with the present invention. Additionally, the present invention is useful for placing the following materials in the root canal space: endodontic medications and medicaments such as calcium hydroxide, chlohexidine, camphorated paramonochlorphenol, formocresol, and camphorated phenol; endodontic sealers such as zinc oxide, calcium hydroxide and resin; and endodontic obturation materials such as gutta percha, and zinc oxide.

While the above description contains many specificities, these should not be construed as limitations on the scope of the invention, but rather as exemplification of certain preferred embodiments. Numerous other variations of the present invention are possible, and is not intended herein to mention all of the possible equivalent forms or ramifications of this invention. Various changes may be made to the present invention without departing from the scope or spirit of the invention.

What is claimed:

1. A device for performing dental procedures, comprising:
    (a) a shaft assembly, said shaft assembly further comprising:
        (i) a threaded housing for attaching said shaft assembly to an ultrasonic generator;
        (ii) an angled shaft connected to said threaded housing, said angled shaft further comprising a bore passing through its length;
        (iii) a hub attached to the end of said angled shaft opposite said threaded housing for reducing the diameter of said bore; and (iv) an aperture passing through the outer wall of said shaft, wherein said aperture is positioned near the larger of the two angles formed by said angled shaft and oriented in the direction of said hub; and (b) a needle for focusing ultrasonic energy, wherein said needle passes through said aperture, said bore in said angled shaft, and exits said shaft through said hub; and (c) a means for delivering fluid through said needle, said means further comprising:
   (i) a reservoir for storing said fluid; and
   (ii) a tubing assembly comprising a length of tubing and a means for connecting said tubing to said reservoir and said needle.

2. The device of claim 1, further comprising an apparatus for generating ultrasonic energy, said apparatus further comprising an attachment means for receiving said threaded housing.

3. The device of claim 1, wherein said reservoir further comprises a syringe.

4. The device of claim 1, wherein said means for connecting said tubing to said reservoir and said needle further comprises Luer-Lok® type connectors mounted on the end of said length of tubing.

5. The device of claim 1, wherein said needle further comprises a substantially non-flexible hypodermic needle, said hypodermic needle further comprising a single, bi-beveled, or tri-beveled tip.

6. The device of claim 1, wherein said needle is stainless steel.

7. The device of claim 1, wherein said angled shaft comprises an angle of about 30° to 90°.

* * * * *